US006471964B1

(12) United States Patent
Biering et al.

(10) Patent No.: US 6,471,964 B1
(45) Date of Patent: Oct. 29, 2002

(54) DNA ENCODING STRUCTURAL PROTEIN-1 OF INFECTIOUS SALMON ANAEMIA VIRUS AND USES THEREOF

(75) Inventors: Eirik Biering, Bergen; Bjørn Krossøy, Nestun, both of (NO)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/690,185

(22) Filed: Oct. 17, 2000

(30) Foreign Application Priority Data

Oct. 18, 1999 (EP) .............................. 99203401

(51) Int. Cl.$^7$ ...................... A61K 39/12; A61K 39/145; C07K 1/00
(52) U.S. Cl. ............................... 424/186.1; 424/209.1; 530/350; 530/300
(58) Field of Search ........................... 424/186.1, 209.1; 530/350, 300

(56) References Cited

FOREIGN PATENT DOCUMENTS

| EP | 0 839 913 | 5/1998 |
| WO | WO 99 27105 | 6/2000 |

OTHER PUBLICATIONS

Jones et al., "Vaccination of Freshwater—reared Atlantic Salmon reduces mortality associated with infectious salmon anaemia virus" Bulletin of the European Associate of Fish Pathologists, vol. 19, No. 3 Jul. 1999, p. 98–101.

Falk et al., "Characterization and applications of a monoclonal antibody against infectious salmon anaemia virus." Diseases of Aquatic Organisms, vol. 34, No. Oct. 1998, p. 77–85.

Falk et al., "Demonstration of Infectious Salmon Anemia (ISA) Viral–Antigens in Cell–Cultures and Tissue–Sections." Veterinary Research, col. 26 No. 5–6, 1995, p. 499–504.

Krossoy et al., "The putative polymerase sequence of infectious salmon anemia virus suggests a new genus with the Orthomyxoviridae" Journal of Virology, Mar. 1999, 73 (3) .p. 2136–42.

Falk et al., "Characterization of infectious salmon anemia virus, an orthomyxo–like virus isolated from Atlantic salmon", Journal of Virology, Dec. 1997, 71 (12) p. 9016–23.

Mjaaland et al., "Genomic characterization of the virus causing infectious salmon anemia in Atlantic salmon: an orthomyxo–like virus in a teleost" Journal of Virology, Oct. 1997, 71 (10) p. 7681–6.

*Primary Examiner*—Hankyel T. Park
*Assistant Examiner*—Stacy Brown
(74) *Attorney, Agent, or Firm*—Mark W. Milstead; William M. Blackstone

(57) ABSTRACT

The present invention concerns a nucleic acid encoding a structural protein of Infectious Salmon Anaemia Virus (ISAV) designated as Structural Protein-1 (SP-1), the isolated SP-1 protein, and use of the nucleic acid and/or protein for diagnostic or vaccine purposes. The invention furthermore pertains to antibodies that are reactive with said SP-1 and their use in diagnostics.

5 Claims, 4 Drawing Sheets

Figure 1:

Immune response of rabbit 716 injected with baculovirus expressed 1H protein

■ Preserum + control antigen    ■ Preserum + ISAV antigen
□ Bleed 31.08.00 + control antigen    □ Bleed 31.08.00 + ISAV antigen

DNA ENCODING STRUCTURAL PROTEIN-1 OF INFECTIOUS SALMON ANAEMIA VIRUS AND USES THEREOF

FIELD OF THE INVENTION

The present invention relates to a nucleic acid encoding a viral structural protein and the use of the nucleic acid or protein for diagnostic or vaccine purposes.

BACKGROUND OF THE INVENTION

Infectious Salmon Anaemia (ISA) is a disease caused by a virus (ISAV) that belongs to the family Orthomyxoviridae. The disease is characterised by severe anaemia, leucopenia, ascites, haemorrhagic liver necrosis and petecchia of the vicera. The gills are pale, and petecchia of the skin is also common. The spleen is dark and swollen (Speilberg et al, 1995; Veterinary Pathology, 32, pp. 466–478). The virus replicates in endothelial cells, both in blood vessels and in the heart, and in polymorphonuclear leukocytes. Budding of the virus from pillar cells in the gills has been observed, indicating that gills are probably an important portal of entrance for ISAV.

ISA was observed for the first time in Norway (Thorud et al., 1988; Bull. Eur. Ass. Fish Pathol., 8 (5), pp. 109–111) and severe outbreaks have recently been diagnosed also in Scotland, the Shetland Islands and Canada. Mortality during outbreaks varies between 10 and 100% and younger individuals appear to be more susceptible than older individuals. However, high mortality has also been observed among market size fish. Clinical outbreaks have been observed so far in Atlantic salmon, but rainbow trout and brown trout may act as carriers of the agent without developing clinical signs. Despite stamping out strategies, new outbreaks occur regularly and result in significant losses.

SUMMARY OF THE INVENTION

Control of the disease therefore has a high priority, and the present invention provides novel means to carry out such control. The present invention provides for a nucleic acid encoding a structural protein, designated Structural Protein-1 (SP-1) of the ISAV and fragments of said protein. The nucleic acid comprises 1851 nucleotides and is depicted in SEQ ID NO 1; the deduced amino acid sequence of SP-1 is depicted in SEQ ID NO 2. The cloning and characterisation of the nucleic acid according to the invention provides for the production of the SP-1 of the ISAV using recombinant technology (Sambrook et al., Molecular cloning: a Laboratory Manual, Cold Spring Harbor Laboratory Press, Cold Spring Harbor, 1989). Cloning techniques and subsequent protein expression using in vitro expression systems are well known in the art. In this way, recombinant SP-1 can be obtained, which is substantially free from other ISAV proteins. SP-1 was found to be specific for the ISA virus, which makes this protein very suitable for use in vaccinations and diagnostics. This isolated SP-1 can be used in the manufacture of vaccines to protect fish against infection with ISA virus. The vaccines may be used as marker vaccine to distinguish vaccination from field infections with ISAV. Alternatively, the nucleic acids encoding the SP-1 can be used to manufacture DNA vaccines or vector vaccines to protect fish against infection with ISAV. The nucleic acids and recombinant proteins of the present invention can furthermore be used for diagnostic purposes, for instance, to detect the presence of the ISAV or anti-ISAV antibodies in fish. Additionally, the recombinant SP-1 of the present invention can be used to produce ISAV specific antibodies. These antibodies can also be used for diagnostic purposes such as for detecting of ISAV in fish.

BRIEF DESCRIPTION OF THE DRAWINGS

FIG. 1 shows an immune response of rabbit 716 injected with baculovirus expressed SP-1 (also referred to as 1H) protein. Preserum=serum taken from rabbit before immunization. Control antigen=control with lysate of non-infected SHK cells. ISAV antigen=lysate of ISAV infected SHK cells. Bleed 31-08-00=antiserum taken 10 days post third immunization.

DETAILED DESCRIPTION OF THE INVENTION

Figure 2:
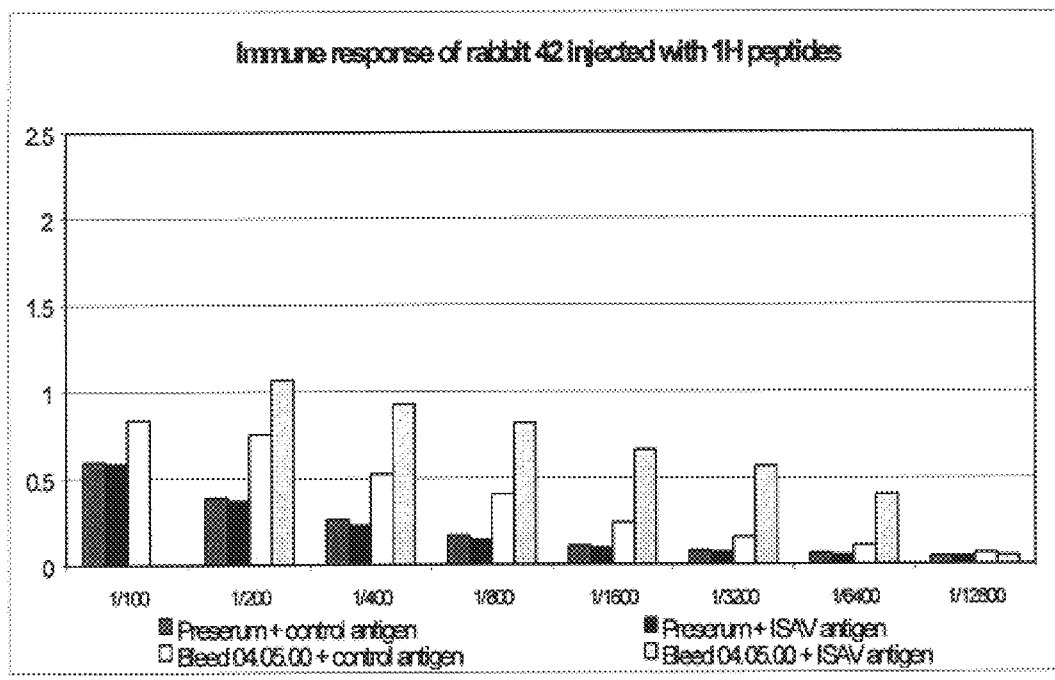
FIG. 2 shows an immune response of rabbit 41 injected with the SP-1 (also referred to as 1H) protein fragment SEQ ID NO 3. Preserum=serum taken from rabbit before immunization. Control antigen=control with lysate of non-infected SHK cells. ISAV antigen=lysate of ISAV infected SHK cells. Bleed 04-05-00=antiserum taken 10 days post third immunization.
Figure 3:
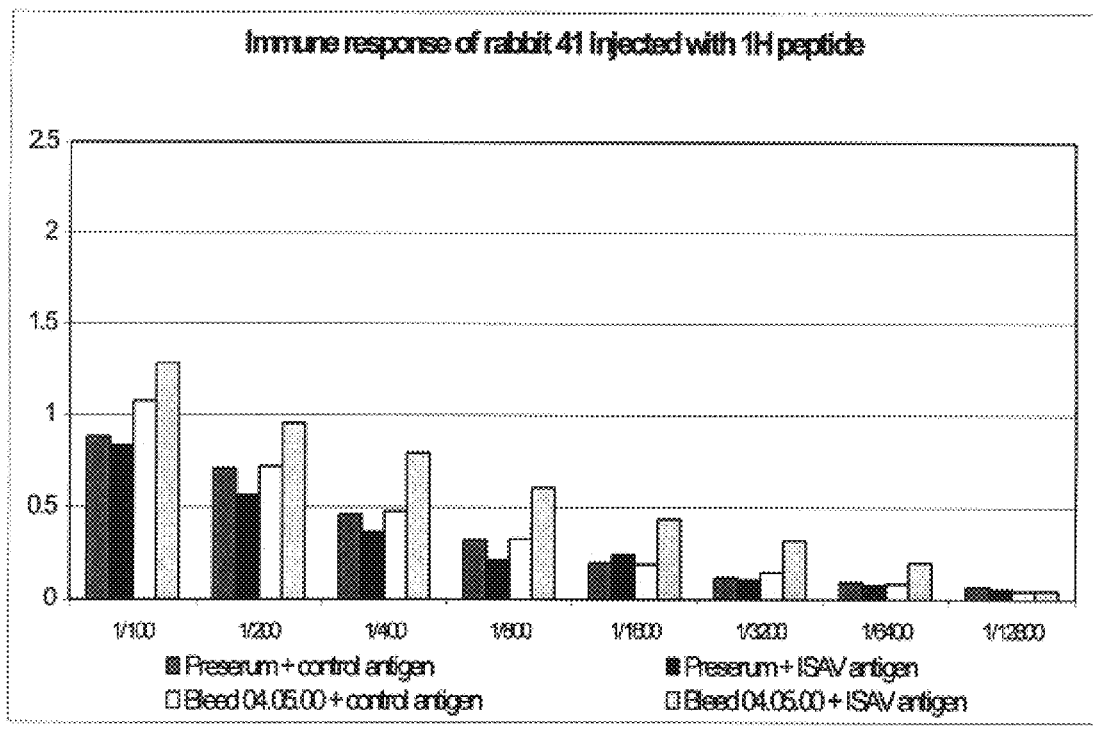
FIG. 3 shows an immune response of rabbit 42 injected with SP-1 (also referred to as 1H) protein fragment SEQ ID NO 4. Preserum=serum taken from rabbit before immunization. Control antigen=control with lysate of non-infected SHK cells. ISAV antigen=lysate of ISAV infected SHK cells. Bleed 04-05-00=antiserum taken 10 days post third immunization.
Figure 4:
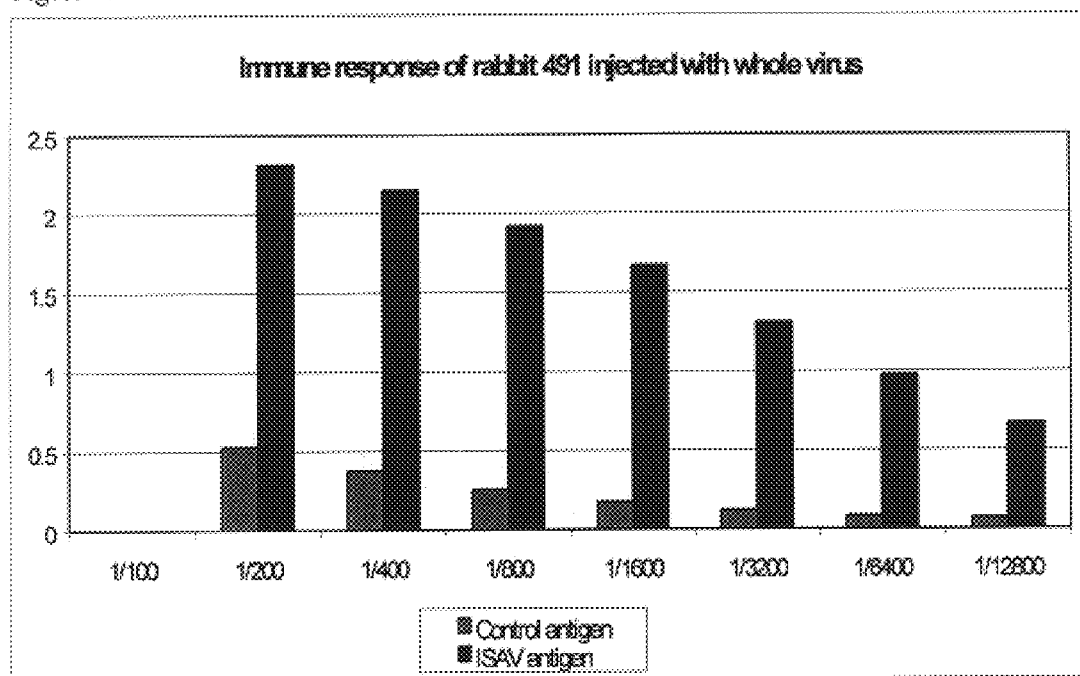
FIG. 4 shows an immune response of rabbit 491 injected with inactivated ISA virus. Control antigen=control with lysate of non-infected SHK cells. ISAV antigen=lysate of ISAV infected SHK cells.

Thus, a first aspect the present invention provides for a nucleic acid comprising the nucleotide sequence depicted in SEQ ID NO 1 encoding the SP-1 protein of ISAV and/or fragments of said nucleotide sequence. Also within the scope of this invention are nucleotide sequences comprising tandem arrays of the sequence depicted in SEQ ID NO 1 or fragments thereof. Nucleotide sequences that are complementary to the sequences depicted in SEQ ID NO 1 or parts thereof are also within the scope of the invention, as well as nucleotide sequence that hybridise with the sequence depicted in SEQ ID NO 1. The hybridisation conditions for this purpose are stringent, preferably highly stringent. According to the present invention the term "stringent" means washing conditions of 1×SSC, 0.1% SDS at a temperature of 65° C.; highly stringent conditions refer to a reduction in SSC concentration towards 0.3×SSC.

Nucleotide sequences that hybridise with the sequence shown in SEQ ID NO 1 are understood to be nucleotide sequences that have a sequence homology of at least 70%, preferably 80%, more preferably 90% with the corresponding matching part of the sequence depicted in SEQ ID NO 1. According to the present invention the sequence homology is determined by comparing the nucleotide sequence with the corresponding part of the sequence depicted in SEQ ID NO 1. The sequence homology between a nucleotide and the sequence in SEQ ID NO 1 can be determined via common sequence analysis program such as BLASTN® and the like. The optimal match area is automatically determined by these programs. Homologous sequences can easily be isolated with the sequence depicted in SEQ ID NO 1 or fragments of this sequence from closely related ISAV strains using routine cloning and hybridisation techniques (Sambrook et al., supra).

The nucleic acids of the invention can be used in the preparation of a DNA vaccine to vaccinate fish against ISA virus infection. DNA vaccination refers to the induction of an immune response to one or more antigens that are expressed in vivo from a gene inserted in a DNA plasmid, which has been inoculated directly into the vaccinated fish.

Thus, in a second aspect of the invention, there is provided for a DNA vaccine comprising a pharmaceutical acceptable DNA plasmid in which one or more nucleic acids according to the invention are operably linked to a transcriptional regulatory sequence.

Preferably the nucleic acids to be used in the DNA plasmid is a nucleic acids comprising the nucleic acids depicted in SEQ ID NO 1, or fragments of said nucleotide sequences. More preferably, the nucleic acid to be used in said DNA plasmid has the nucleic acids depicted in SEQ ID NO 1. Also suitable for use in said DNA plasmid are nucleic acids having sequences that are complementary to the sequence of SEQ ID NO 1 or having sequences that hybridise with the sequence of SEQ ID NO 1. The sequence homology between the nucleotide sequences that hybridise with the sequence of SEQ ID NO 1 is determined as described earlier.

DNA plasmids that are suitable for use in a DNA vaccine according to the invention are conventional cloning or expression plasmids for bacterial, eukaryotic and yeast host cells, many of which are commercially available. Well-known examples of such plasmids are pBR322 and pcDNA3 (Invitrogen). The DNA plasmids according to the invention should be able to induce protein expression of the nucleotide sequences. The DNA plasmid can comprise one or more nucleic acids according to the invention. In addition, the DNA plasmid can comprise other nucleic acids such as the immune-stimulating oligonucleotides having unmethylated CpG dinucleotides, or nucleic acids having sequences that code for other antigenic proteins or adjuvating cytokines.

Transcriptional regulatory sequences that are suitable for use in a DNA plasmid according to the invention comprise promoters such as the (human) cytomegalovirus immediate early promoter (Seed, B. et al., Nature 329, 840–842, 1987; Fynan, E. F. et al., PNAS 90, 11478–11482, 1993; Ulmer, J. B. et al., Science 259, 1745–1748, 1993), Rous sarcoma virus LTR (RSV, Gorman, C. M. et al., PNAS 79, 6777–6781, 1982; Fynan et al., supra; Ulmer et al., supra), the MPSV LTR (Stacey et al., J. Virology 50, 725–732, 1984), SV40 immediate early promoter (Sprague J. et al., J. Virology 45, 773, 1983), the metallothionein promoter (Brinster, R. L. et al., Nature 296, 39–42, 1982), the major late promoter of Ad2, the β-actin promoter (Tang et al., Nature 356, 152–154, 1992). The regulatory sequences may also include terminator and polyadenylation sequences. Amongst the sequences that can be used are the well-known bovine growth hormone polyadenylation sequence, the SV40 polyadenylation sequence, the human cytomegalovirus (hCMV) terminator and polyadenylation sequences.

The DNA plasmid comprising a nucleic acid according to the present invention operably linked to a transcriptional regulatory sequence for use in the vaccine according to the invention can be naked or can be packaged in a delivery system. Suitable delivery systems are lipid vesicles, Iscoms, dendromers, niosomes, polysaccharide matrices, and the like. Also very suitable as a delivery system is an attenuated live bacteria such as Salmonella.

The nucleic acids according to the invention can also be used in the production of a vector vaccine to vaccinate fish against ISA virus infection. A vector vaccine is understood to be a vaccine in which a live, attenuated bacteria or virus has been modified so that it contains one or more heterologous nucleotide sequences inserted into its genetic material. These so called vector bacteria or viruses are capable of coexpressing the heterologous proteins encoded by the inserted nucleotides.

Thus, a third aspect the invention provides for a vector vaccine comprising a live attenuated bacteria or virus which has been modified to comprise in their genetic material one or more of the nucleic acids of the present invention.

Preferably the nucleic acids to be used in said vector vaccine comprises the nucleotide sequences depicted in SEQ ID NO 1, or fragments of the nucleotide sequence. More preferably the nucleic acid to be used in a vector vaccine according to the invention has the nucleic acids depicted in SEQ ID NO 1. Also suitable for use in said vector vaccine are nucleic acids having sequences that are complementary to the sequence of SEQ ID NO 1 or having nucleotide sequences that hybridise with the sequence of SEQ ID NO 1. The sequence homology between the nucleotide sequences that hybridise with the sequence of SEQ ID NO 1 is determined as described earlier.

Very suitable for use as a vaccine vector is, for example, vaccinia virus or Semliki forest virus.

In a fourth aspect, the nucleic acids according to the invention can be used for the recombinant production of the Structural Protein-1, substantially free from other ISAV proteins. Thus, the invention provides for a SP-1 protein encoded by a nucleic acid according to the present invention. More specifically, the invention provides for an SP-1 protein comprising an amino acid sequence as depicted in SEQ ID NO 2 and/or a derivative of the amino acid sequence.

SP-1 proteins comprising an amino acid sequence that is a derivative of the sequence depicted in SEQ ID NO 2 are understood to be proteins which have alterations in their amino acid sequence with respect to the amino acid sequence depicted in SEQ ID NO 2 which do not affect the antigenic or immunogenic characteristics of the SP-1.

For the purpose of this invention, antigenic characteristics of the SP-1 protein are understood to be the ability to induce production of antibodies that recognise and (cross)-react with the ISA virus. Immunogenic characteristics are understood to be the ability to induce an immune response in fish that protects against infection with ISA virus.

The alterations that can occur in a sequence according to the present invention could, for instance, result from conservative amino acid substitutions, deletions, insertions, inversions or additions of (an) amino acid(s) in the overall sequence. Amino acid substitutions that are expected not to alter the immunological properties have been described. Amino acid replacements between related amino acids or replacements which have occurred frequently in evolution are, inter alia, Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information, Lipman and Pearson developed a method for rapid and sensitive protein comparison (Science, 1985, vol. 227, 1435–1441) and determining the functional similarity between proteins and peptides having sequence homology.

The derivative proteins according to the invention are still able to function as the native SP-1 and/or induce production of antibodies that recognise and (cross)-react with the ISA virus. Other derivatives according to the present invention are protein fragments that are still capable of inducing production of antibodies that recognise and (cross)-react with ISA virus or of inducing an immune response in fish that protects against infection with ISA virus. Preferably a protein according to the invention has the amino acid sequence depicted in SEQ ID NO 2 or a fragment thereof. Suitable fragments according to the invention have the amino acid sequence SRPKRSDYRKGQGSKC (SEQ ID NO 3) or CIEFDEDDQEEEDTDI (SEQ ID NO 4).

The proteins according to the invention can be prepared via standard recombinant protein expression techniques. For this purpose a nucleic acid according to the invention encoding SP-1, a derivative protein of SP-1 or a multimere of SP-1 is inserted into an expression vector. Preferably the nucleic acid comprises the nucleic acids depicted in SEQ ID NO 1 or one or more fragments thereof. Also suitable are nucleic acids having sequences that are complementary to the sequence of SEQ ID NO 1 sequences of which the sequence homology with the sequence depicted in SEQ ID NO 1 is at least 70%, preferably 80%, and more preferably 90%. The sequence homology between the nucleic acidss that are suitable for use in the DNA plasmid is determined as described earlier.

Suitable expression vectors are, amongst others, plasmids, cosmids, viruses and YAC's (Yeast Artificial Chromosomes) which comprise the necessary control regions for replication and expression. The expression vector can be brought to expression in a host cell. Suitable host cells include but are not limited to bacteria, yeast cells, insect cells and mammalian cells. Such expression techniques are well known in the art (Sambrooke et al., Molecular Cloning: a Laboratory Manual, Cold Spring Harbor Laboratory Press, Cold Spring Harbor, 1989). Following expression, the expressed proteins can be isolated and purified from the medium.

In a further aspect, the invention provides for a vaccine comprising a protein according to the present invention and a pharmaceutically acceptable carrier. More specifically, a vaccine according to the invention comprises a protein comprising an amino acid sequence depicted in SEQ ID NO 2 and/or a derivative of said amino acid sequence. Preferably a vaccine according to the invention comprises a protein having the amino acid sequence depicted in SEQ ID NO 2 or a protein fragment having the amino acid sequence depicted in SEQ ID NO 3 or 4.

Vaccines according to the invention can be prepared according to techniques well known to the skilled practitioner. Vaccines according to the invention comprise an effective amount of an immunogen according to the invention and a pharmaceutically acceptable carrier. The term "effective " as used herein is defined as the amount sufficient to induce an immune response in the target fish. An immunogen according to the invention comprises a DNA plasmid in which one or more nucleic acids according to the invention are operably linked to a transcriptional regulatory sequence, a vaccine vector comprising one or more nucleic acids according to the invention, or a protein according to the invention. The amount of plasmid, vector or protein will depend on the type of plasmid or vector, the route of administration, the time of administration, the species of the fish as well as age, general health and diet.

In general, a dosage of 0.01 to 1000 µg protein per kg body weight, preferably 0.5 to 500, more preferably 0.1 to 100 µg protein can be used. With respect to the DNA vaccines, generally a minimum dosage of 10 pg. up to dosages of 1000 µg have been described to be sufficient for a suitable expression of the antigens in vivo.

Pharmaceutically acceptable carriers that are suitable for use in a vaccine according to the invention are sterile water, saline, aqueous buffers such as PBS and the like. In addition, a vaccine according to the invention may comprise other additives such as adjuvants, stabilisers, anti-oxidants and others.

Suitable adjuvants include, amongst others, aluminium hydroxide, aluminium phosphate, amphigen, tocophenols, monophosphenyl lipid A, muramyl dipeptide, oil emulsions, glucans, cytokines and saponins such as QUILL A®. The amount of adjuvant added depends on the nature of the adjuvant itself.

Suitable stabilisers for use in a vaccine according to the invention are, for example, carbohydrates including sorbitol, mannitol, starch, sucrose, dextrin, and glucose, proteins such as albumin or casein, and buffers like alkaline phosphates.

The vaccines according to the invention are administered to the fish via injection, spray, immersion or per oral. The administration protocol can be optimised in accordance with standard vaccination practice.

The nucleic acids and the proteins according to the invention are also suitable for use in diagnostics. The nucleic acids or fragments thereof can be used to detect the presence of ISAV in fish. A sample of fish infected with ISAV will comprise nucleic acid material derived from said virus, including nucleic acid sequences encoding for a protein according to the invention. Suitable methods for the detection of nucleic acids that are reactive with the nucleic acids of the present invention include hybridisation techniques including but not limited to PCR techniques and NASBA techniques.

Fragments of the nucleic acids according to the present invention can be used as primer or probe for the detection of ISAV specific nucleic acids. To be suitable for use as a primer, a fragment according to the invention should constitute at least 18 consecutive nucleotides, more preferably 25 consecutive nucleotides of a nucleic acids according to the invention. Examples of such suitable fragments are 5'-CAG GTG GGA GTG GCA TGG-3' (SEQ ID NO 5) as forward primer and 5'-AGA CTT GGC TCC TTC CGG TG-3' (SEQ ID NO 6) as reverse primer. The primers according to the invention can be used to obtain a probe for use in northern or southern blotting techniques to detect the presence of ISA virus. For this purpose, a probe should contain at least 100, more preferably at least 200 consecutive nucleotide residues of a nucleotide sequence according to the invention. The primer pair having nucleotide sequences SEQ ID NO's 5 and 6 was used to obtain a probe of 626 nucleotides by PCR. This probe resembles 626 consecutive nucleotides of the SP-1 gene of ISA virus and hybridizes specifically to the SP-1 RNA derived from ISAV. Primers and probes according to the invention can be produced using standard genetic engeneering techniques. The nucleic acids depicted in SEQ ID NO 1 is specific for the ISA virus; hence primers and probes based on this nucleic acids will specifically detect RNA or DNA sequences from ISA virus.

The proteins according to the present invention can be used to detect the presence of anti-SP-1 -antibodies in fish. Since SP-1 is characteristic of the ISA virus, the presence of antibodies against the SP-1 in fish is an indication of infection with ISA virus. In general, these antibodies can be detected by an immunoassay comprising the steps of:
(i) incubating a sample suspected of containing antibodies against ISAV with SP-1 antigen,
(ii) allowing the formation of antibody-antigen complex, and
(ii) detecting the presence of the antibody-antigen complex.

The design of this immunoassay may vary. For example, the immunoassay may be based upon competition or direct reaction. Furthermore, protocols may use solid supports or may use cellular material. The detection of the antibody-antigen complex may involve the use of labelled antibodies; the labels may be, for example, enzymes, fluorescent-, chemiluminescent-, radioactive or dye molecules.

Suitable methods for the detection of antibodies reactive with a protein according to the present invention in the sample include the enzyme-linked immunosorbent assay (ELISA), immunofluorescent test (IFT) and Western blot analysis.

The proteins according to the invention can also be used for the production of antibodies, using the general techniques available to the practitioner in the field. Antibodies that are produced with a protein according to the invention have the advantage of specifically reacting with SP-1 of ISA virus. Preferably the proteins are used to produce specific monoclonal antibodies. The obtained antibodies may be utilised in diagnostics also, to detect the presence of ISAV in the fish.

Thus, in another aspect, the present invention provides for a diagnostic kit comprising a suitable means for detection and one or more nucleic acids according to the invention, or one or more proteins according to the invention, or antibodies obtained with said proteins, respectively.

Antibodies according to the invention can be prepared according to standard techniques. Procedures for immunising animals, e.g. mice with proteins and selection of hybridomas producing immunogen specific monoclonal antibodies are well known in the art (see for example Coligan et al. (eds), Current protocols in Immunology, 1992; Kohler and Milstein, Nature 256:495–497, 1975; Steenbakkers et al., Mol. Biol. Rep. 19:125–134, 1994). The antibody is preferably a monoclonal antibody.

The following examples are illustrative of the present invention but should not be interpreted as limiting the invention.

EXAMPLE 1
Virus Isolation and Construction of cDNA Library

Kidney samples were taken from Atlantic salmon (*Salmo salar L.*) during an outbreak of ISA at Bremnes (Norway) in 1998. The samples were homogenized and cleared by centrifugation before filtration (0.2 µm). The homogenates were diluted 1:100 in phosphate buffered saline and incubated for 3 h at 15° C. in cell culture flasks with mono layers of ASK (Atlantic Salmon Kidney) cells. The inoculum was then replaced by cell culture medium (L-15 supplemented with 5% FCS, 50 µg ml$^{-1}$ gentamycin and 4 mM L-glutamine) and the cultures were incubated at 15° C. RNA was isolated from ISAV infected ASK cells using the Trizol reagent (Life Technologies). Cells were infected with ISAV and total RNA was isolated at days 2, 3 and 4 post infection. The RNA was pooled and 2 µg was used for cDNA synthesis with the cDNA Synthesis Kit (Stratagene). A unidirectional bacteriophage Lambda cDNA library was then constructed using the Uni-ZAP XR vector and Gigapack III Gold packaging extract (Stratagene).

EXAMPLE 2
Screening of Bacteriophage Lambda cDNA Library

SP-1 was identified by immunoscreening with a polyclonal anti ISAV rabbit sera (see below) using the picoBlue Immunoscreening Kit (Stratagene). PCR products from clones suspected to be ISAV derived were produced using vector primers and the products were sequenced. One set of internal PCR primers was constructed for each sequence, and this primer pair was employed on cDNA from ISAV infected cells and uninfected cells to determine whether the sequence was viral. The pBlueScript plasmid was then excised from ISAV positive clones using the ExAssist helper phage and the SOLR strain of *E. coli* (Stratagene). Complete sequencing was performed on the isolated plasmids. To obtain full-length cDNA sequences, 5' RACE was performed with the 5'RACE System, Version 2.0 (Life Technologies). RACE products were cloned into the pCR 2.1-TOPO vector using the TOPO TA Cloning Kit (Invitrogen) and sequenced as described below.

DNA Sequencing and Assembly

EXAMPLE 3

Plasmids and PCR products were sequenced using the BigDye Terminator Sequencing Kit and an ABI 377 DNA analyzer (PE Biosystems). Sequences were assembled with the Sequencher software (Gene Codes Corporation). GeneBank searches were done with BLAST (2.0).

EXAMPLE 4
Preparation of Antisera

ISAV virions were purified on a continuous sucrose gradient as described in Mjaaland et al. J. Virol. 71. p. 7681–7686, 1997. Polyclonal antisera were prepared by immunizing rabbits three times with six weeks intervals using approximately 50 µg of purified ISAV for each immunization. The first and second immunizations was administered subcutaneously in Freund's complete and Freund's incomplete adjuvants (Difco) respectively. The third immunization was administered intravenously in saline. The animals were bled 10 days post third immunization. Peptide antisera were prepared against the predicted SP-1 protein by Eurogentec (Belgium) using the peptides SRPKRS-DYRKGQGSKC (SEQ ID NO 3) and CIEFDED-DQEEEDTDI (SEQ ID NO 4) coupled to keyhole limpet haemocyanin. The conjugated peptides were pooled and injected in two rabbits according to Eurogentec's procedures.

EXAMPLE 5
Northern Blot Analysis

Northern blotting was performed with the Northern Max Kit (Ambion). Briefly, approx. 15 µg of total RNA from ISAV infected ASK cells (3 days post infection) or from uninfected cells were separated by formaldehyde-agarose gel electrophoresis and blotted onto Hybond N nylon membranes (Amersham Pharmacia Biotech). Probes were prepared and used according to the DIG High Prime Labeling and Detection Starter Kit 2 (Boehringer Mannheim). The DIG Labeled RNA molecular weight marker 1 (Boehringer Mannheim) was run in parallel.

EXAMPLE 6
Baculovirus Expression of SP-1 cDNA

SP-1 cDNA was amplified using primers 5'-cgggatccatggccgataaaggtatgac-3' (SEQ ID NO 7) and 5'-ggggtacctgcagtttcaaatgtcagtgtc-3' (SEQ ID NO 8) and cloned into the Bam HI and Kpn I sites of pFastBac1 (Life Technologies). The construct was transformed into TOP 10 cells (Invitrogen) and the isolated plasmid were used to transform DH10Bac competent cells (Life Technologies). Recombinant baculoviruses were constructed according to Life Technologies' recommendations.

EXAMPLE 7
Immunofluorescence on Sf9 Cells

Sf9 cells infected with SP-1-recombinant or non-recombinant baculovirus were grown in microtiter plates at 28° C. At 5 days post infection, the cells were fixed in 96% ethanol and air dried. Cells were incubated with the polyclonal rabbit antiserum for 1 hour at 37° C. After washing with PBS, fluorescein isothiocyanate conjugated goat α rabbit IgG (KPL) was added, and cells were incubated at 37° C. for 1 hour. After washing, the cells were mounted with glycerol-saline and examined using an ultra violet microscope.

EXAMPLE 8

SDS-PAGE and Western Blotting

Lysates of Sf9 cells or purified ISAV were separated on discontinuous SDS-PAGE gels (4% stacking and 12% separating gels) at 200 V for 40 min. Proteins were blotted onto nitrocellulose by electrophoresis at 100 V for 60 min. After blocking and washing, the membranes were incubated with peptide sera (diluted 1: X) or polyclonal antisera (diluted (1:x) followed by a peroxidase conjugated goat α rabbit IgG serum (BioRad) diluted 1:X.

EXAMPLE 9

ELISA

Lysates of ISAV infected and non-infected (control) SHK cells were diluted in carbonate-bicarbonate buffer (15 mM $Na_2CO_3$, 35 mM $NaHCO_3$, pH 9.6) to a total protein concentration of 5 µg ml$^{-1}$. Microtitre plates (96 wells, Nunc) were coated overnight at 4° C. with 100 µl/well and washed 5 times with phosphate-buffered saline (0.1M, pH 7.2) containing 0.1% Tween-20 (PBS-Tween). The plates were post-coated (150 RI) with 5% fat-free dried milk in PBS-Tween for 1 h at 20° C. and washed 5 times with PBS-Tween. All subsequent incubations were carried out in PBS-Tween containing 0.5% fat-free dried milk. A dilution series of serum samples (100 µl) was incubated at 4° C. overnight followed by washing 5 times with PBS-Tween. 100 µl of horseradish-peroxidase conjugated goat-anti-rabbit serum (Amersham) diluted 1:2000 were incubated for 45 min at 20° C. After washing 3 times with PBS-Tween and 2 times with PBS, the binding was visualised using 100 µl o-phenylenediamine dihydrochloride (OPD, Sigma) solution (0.4 mg/ml OPD in phosphate citrate buffer, pH 5.0). The reaction was stopped after 20 min by the addition of 100 µl 2.3 M $H_2SO_4$. After equilibration for 30 min at 4° C., the plates were read at 492 nm in a Titertec Multiscan SSC spectrophotometer.

EXAMPLE 10

Vaccination

Lysate of Sf9 cells infected with SP-1-recombinant baculovirus were emulgated in a non-mineral oil and injected into Atlantic salmon (*Salmo salar*) presmolts. Control fish were injected with saline or a vaccine based upon inactivated ISAV previously shown to be effective. The fish were kept in individual tanks, and challenged 10 weeks post vaccination by intra peritoneal injection of ISAV Bremnes 98.

EXAMPLE 11

Cloning and Sequence Determination of an ISAV cDNA

Immunoscreening of the bacteriophage Lambda cDNA library with the polyclonal serum prepared against whole virus identified a possible ISAV clone with an open reading frame (ORF) of 1851 bases. The clone was tentatively designated SP-1. The SP-1 ORF encodes a protein with predicted molecular weight of 68.1 kDa. SP-1 specific PCR primers amplified a product from ISAV infected ASK cells and not from uninfected cells. Also, a DIG labeled SP-1 specific DNA probe prepared using the same primers hybridized with total RNA from ISAV infected ASK cells and not with RNA from uninfected cells. This clearly demonstrates that the SP-1 sequence is ISAV derived and not of cellular origin. Also, primers and probes complementary to the SP-1 sequence are useful as diagnostic tools for ISA.

Expression of SP-1 and Identification of Gene Products

EXAMPLE 12

Expression of the SP-1 cDNA in baculovirus infected Sf9 cells resulted in a protein with molecular weight approximately 70 kDa that reacted with the polyclonal antiserum prepared against whole virus and with the peptide serum in Western blotting. Lysate of Sf9 cells infected with baculovirus without insert was negative. The polyclonal serum also reacted with a similar protein in purified virus. The polyclonal antiserum and the peptide serum also reacted with Sf9 cells infected with SP-1-recombinant baculovirus in IFAT but not with cells infected with empty baculovirus. These results show that a viral protein has been expressed in the baculovirus system and that rabbit anti-sera raised against the specified SP-1 peptides is useful to detect the presence of ISAV.

Detection of Immune Response in Rabbits Against Baculovirus Expressed SP-1 Protein

EXAMPLE 13

Immunization of rabbits with baculovirus expressed SP-1 Protein (FIG. 1) or SP-1 corresponding peptides conjugated to keyhole limpet haemocyanin (FIGS. 2 and 3), induced an immune response and production of ISAV reactive antibodies. The response following injection of baculovirus expressed SP-1 protein was comparable to the response obtained in rabbits immunized with whole virus (FIG. 4). These results show that baculovirus expressed SP-1 protein or synthetic peptides from the SP-1 sequence is immunogenic in rabbits and induce an immune response directed against the wild type ISAV. The obtained antisera are useful as diagnostic tools. Furthermore, the results indicate that the SP-1 protein or synthetic peptides from the sequence will be useful in a vaccine against ISAV.

What is claimed is:

1. An isolated protein comprising an amino acid sequence according to SEQ ID NO 2 or a derivative thereof, wherein the derivative thereof has antigenic or immunogenic characteristics of the amino acid sequence according to SEQ ID NO 2.

2. A vaccine comprising a protein according to claim 1 and a pharmaceutically acceptable carrier.

3. A pharmaceutical composition comprising a protein according to claim 1, and a pharmaceutically acceptable carrier.

4. A diagnostic composition comprising a protein of claim 1.

5. A diagnostic kit comprising a suitable detection means and a protein according to claim 1.

* * * * *

SEQUENCE LISTING

```
<160> NUMBER OF SEQ ID NOS: 8

<210> SEQ ID NO 1
<211> LENGTH: 1851
<212> TYPE: DNA
<213> ORGANISM: Infectious salmon anemia virus
<220> FEATURE:
<221> NAME/KEY: CDS
```

<222> LOCATION: (1)..(1851)

<400> SEQUENCE: 1

```
atg gcc gat aaa ggt atg act tat tct ttt gat gtc aga gac aac acc      48
Met Ala Asp Lys Gly Met Thr Tyr Ser Phe Asp Val Arg Asp Asn Thr
 1               5                  10                  15 ttg gtt gta aga aga tct acc gct act aaa agt ggt ata aag atc tcc      96
Leu Val Val Arg Arg Ser Thr Ala Thr Lys Ser Gly Ile Lys Ile Ser
             20                  25                  30 tac aga gaa gat aga ggt act tca ctt ctc caa aag gcc ttt gcg ggg     144
Tyr Arg Glu Asp Arg Gly Thr Ser Leu Leu Gln Lys Ala Phe Ala Gly
         35                  40                  45 aca gat gat gaa ttc tgg ctg gag ctg gat caa gac gtg tac gta gac     192
Thr Asp Asp Glu Phe Trp Leu Glu Leu Asp Gln Asp Val Tyr Val Asp
     50                  55                  60 aag agg att aga aag ttc ctt gag gaa gag aag atg aag gac atg agc     240
Lys Arg Ile Arg Lys Phe Leu Glu Glu Glu Lys Met Lys Asp Met Ser
 65                  70                  75                  80 ccc aga tgt tct ggt tct gtt gct gca gca atc gaa agg tca gtg gag     288
Pro Arg Cys Ser Gly Ser Val Ala Ala Ala Ile Glu Arg Ser Val Glu
                 85                  90                  95 ttc gac aac ttt tca aag gaa gca gct gcg aac atc gag atg tca gga     336
Phe Asp Asn Phe Ser Lys Glu Ala Ala Ala Asn Ile Glu Met Ser Gly
            100                 105                 110 gag gac gag gaa gaa gca ggt ggg agt ggc atg gtt gac aac aag agg     384
Glu Asp Glu Glu Glu Ala Gly Gly Ser Gly Met Val Asp Asn Lys Arg
        115                 120                 125 agg aac aaa ggg gtc tcc aac atg gcg tac aac ctt tca ctg ttc att     432
Arg Asn Lys Gly Val Ser Asn Met Ala Tyr Asn Leu Ser Leu Phe Ile
    130                 135                 140 gga atg gtc ttc cct gca atc acc acg ttc ttc agc gca atc ctg tca     480
Gly Met Val Phe Pro Ala Ile Thr Thr Phe Phe Ser Ala Ile Leu Ser
145                 150                 155                 160 gaa ggt gaa atg agc atc tgg caa aac ggg cag gca atc atg agg att     528
Glu Gly Glu Met Ser Ile Trp Gln Asn Gly Gln Ala Ile Met Arg Ile
                165                 170                 175 ctc gct ttg gct gat gaa gac gga aag agg caa acg aga aca ggc gga     576
Leu Ala Leu Ala Asp Glu Asp Gly Lys Arg Gln Thr Arg Thr Gly Gly
            180                 185                 190 cag aga gtg gac atg gca gat gtt acc aag cta aac gtg gtg aca gca     624
Gln Arg Val Asp Met Ala Asp Val Thr Lys Leu Asn Val Val Thr Ala
        195                 200                 205 aac ggg aaa gtc aag cag gtt gaa gtc aat ttg aat gac ctg aag gca     672
Asn Gly Lys Val Lys Gln Val Glu Val Asn Leu Asn Asp Leu Lys Ala
    210                 215                 220 gct ttc aga cag agc aga ccc aaa agg tca gac tac agg aaa gga caa     720
Ala Phe Arg Gln Ser Arg Pro Lys Arg Ser Asp Tyr Arg Lys Gly Gln
225                 230                 235                 240 gga tca aag gca act gaa tca agt att tcc aac cag tgc atg gct ctg     768
Gly Ser Lys Ala Thr Glu Ser Ser Ile Ser Asn Gln Cys Met Ala Leu
                245                 250                 255 att atg aag tca gtg ttg tca gca gac cag ctg ttt gca cca ggt gtg     816
Ile Met Lys Ser Val Leu Ser Ala Asp Gln Leu Phe Ala Pro Gly Val
            260                 265                 270 aag atg atg agg acc aat ggt ttc aac gca tca tac act aca cta gca     864
Lys Met Met Arg Thr Asn Gly Phe Asn Ala Ser Tyr Thr Thr Leu Ala
        275                 280                 285 gaa gga gcc aac att cca agc aag tac cta agg cac atg agg aac tgc     912
Glu Gly Ala Asn Ile Pro Ser Lys Tyr Leu Arg His Met Arg Asn Cys
    290                 295                 300
```

-continued

```
gga gga gtt gct ctg gat ctt atg gga atg aag agg atc aag aat tca        960
Gly Gly Val Ala Leu Asp Leu Met Gly Met Lys Arg Ile Lys Asn Ser
305                 310                 315                 320 ccg gaa gga gcc aag tct aag atc ttt tct atc atc cag aag aaa gtc       1008
Pro Glu Gly Ala Lys Ser Lys Ile Phe Ser Ile Ile Gln Lys Lys Val
                325                 330                 335 agg gga agg tgt cgc act gag gag caa cgg ctg ctg act agt gca ttg       1056
Arg Gly Arg Cys Arg Thr Glu Glu Gln Arg Leu Leu Thr Ser Ala Leu
            340                 345                 350 aag atc agt gat ggc gag aac aag ttc caa agg atc atg gac act ctg       1104
Lys Ile Ser Asp Gly Glu Asn Lys Phe Gln Arg Ile Met Asp Thr Leu
        355                 360                 365 tgc aca agc ttt ctg att gac cca cct aga aca acc aaa tgc ttc att       1152
Cys Thr Ser Phe Leu Ile Asp Pro Pro Arg Thr Thr Lys Cys Phe Ile
    370                 375                 380 cca cct atc tcc agt ctc ttg acg tac att cag gac gga aat tca gtg       1200
Pro Pro Ile Ser Ser Leu Leu Thr Tyr Ile Gln Asp Gly Asn Ser Val
385                 390                 395                 400 ttg gca atg gac ttc atg aag aac gga gaa gat gct tgc agg atc tgc       1248
Leu Ala Met Asp Phe Met Lys Asn Gly Glu Asp Ala Cys Arg Ile Cys
                405                 410                 415 aga gag gca aag ctg aag gtt gga gtg aac ggc aca ttc aca atg tct       1296
Arg Glu Ala Lys Leu Lys Val Gly Val Asn Gly Thr Phe Thr Met Ser
            420                 425                 430 gtg gct aga aca tgt gta gct gtg tca atg gtt gca aca gca ttc tgt       1344
Val Ala Arg Thr Cys Val Ala Val Ser Met Val Ala Thr Ala Phe Cys
        435                 440                 445 tca gca gac atc atc gag aat gca gtt cct ggc tcg gaa agg tac agg       1392
Ser Ala Asp Ile Ile Glu Asn Ala Val Pro Gly Ser Glu Arg Tyr Arg
    450                 455                 460 tca aac atc aag gca aac aca acc aaa ccc aag aag gac tca aca tac       1440
Ser Asn Ile Lys Ala Asn Thr Thr Lys Pro Lys Lys Asp Ser Thr Tyr
465                 470                 475                 480 aca atc caa ggg ctg agg ctg tcc aat gtg aag tac gag gca aga cct       1488
Thr Ile Gln Gly Leu Arg Leu Ser Asn Val Lys Tyr Glu Ala Arg Pro
                485                 490                 495 gaa aca tct caa agc aac aca gat cga agc tgg caa gta aat gtc aca       1536
Glu Thr Ser Gln Ser Asn Thr Asp Arg Ser Trp Gln Val Asn Val Thr
            500                 505                 510 gac agt ttc gga ggg cta gcg gtt ttc aac caa ggc gct atc agg gag       1584
Asp Ser Phe Gly Gly Leu Ala Val Phe Asn Gln Gly Ala Ile Arg Glu
        515                 520                 525 atg ctt gga gat gga aca tct gag aca aca agt gtg aat gtc agg gct       1632
Met Leu Gly Asp Gly Thr Ser Glu Thr Thr Ser Val Asn Val Arg Ala
    530                 535                 540 ctg gta aag agg atc ttg aag tct gct tca gaa aga agc gca aga gct       1680
Leu Val Lys Arg Ile Leu Lys Ser Ala Ser Glu Arg Ser Ala Arg Ala
545                 550                 555                 560 gta aag aca ttc atg gtt gga gaa caa ggg aag tct gca att gtt atc       1728
Val Lys Thr Phe Met Val Gly Glu Gln Gly Lys Ser Ala Ile Val Ile
                565                 570                 575 tca gga gtg ggg ctt ttc tct att gac ttt gaa ggg gtt gag gag gca       1776
Ser Gly Val Gly Leu Phe Ser Ile Asp Phe Glu Gly Val Glu Glu Ala
            580                 585                 590 gag agg atc act gac atg aca cct gac atc gag ttc gat gag gac gat       1824
Glu Arg Ile Thr Asp Met Thr Pro Asp Ile Glu Phe Asp Glu Asp Asp
        595                 600                 605 cag gag gag gaa gac act gac att tga                                    1851
Gln Glu Glu Glu Asp Thr Asp Ile
```

-continued

```
    610                 615

<210> SEQ ID NO 2
<211> LENGTH: 616
<212> TYPE: PRT
<213> ORGANISM: Infectious salmon anemia virus

<400> SEQUENCE: 2

Met Ala Asp Lys Gly Met Thr Tyr Ser Phe Asp Val Arg Asp Asn Thr
  1               5                  10                  15

Leu Val Val Arg Arg Ser Thr Ala Thr Lys Ser Gly Ile Lys Ile Ser
             20                  25                  30

Tyr Arg Glu Asp Arg Gly Thr Ser Leu Leu Gln Lys Ala Phe Ala Gly
         35                  40                  45

Thr Asp Asp Glu Phe Trp Leu Glu Leu Asp Gln Asp Val Tyr Val Asp
     50                  55                  60

Lys Arg Ile Arg Lys Phe Leu Glu Glu Glu Lys Met Lys Asp Met Ser
 65                  70                  75                  80

Pro Arg Cys Ser Gly Ser Val Ala Ala Ala Ile Glu Arg Ser Val Glu
                 85                  90                  95

Phe Asp Asn Phe Ser Lys Glu Ala Ala Ala Asn Ile Glu Met Ser Gly
            100                 105                 110

Glu Asp Glu Glu Glu Ala Gly Gly Ser Gly Met Val Asp Asn Lys Arg
        115                 120                 125

Arg Asn Lys Gly Val Ser Asn Met Ala Tyr Asn Leu Ser Leu Phe Ile
    130                 135                 140

Gly Met Val Phe Pro Ala Ile Thr Thr Phe Phe Ser Ala Ile Leu Ser
145                 150                 155                 160

Glu Gly Glu Met Ser Ile Trp Gln Asn Gly Gln Ala Ile Met Arg Ile
                165                 170                 175

Leu Ala Leu Ala Asp Glu Asp Gly Lys Arg Gln Thr Arg Thr Gly Gly
            180                 185                 190

Gln Arg Val Asp Met Ala Asp Val Thr Lys Leu Asn Val Val Thr Ala
        195                 200                 205

Asn Gly Lys Val Lys Gln Val Glu Val Asn Leu Asn Asp Leu Lys Ala
    210                 215                 220

Ala Phe Arg Gln Ser Arg Pro Lys Arg Ser Asp Tyr Arg Lys Gly Gln
225                 230                 235                 240

Gly Ser Lys Ala Thr Glu Ser Ser Ile Ser Asn Gln Cys Met Ala Leu
                245                 250                 255

Ile Met Lys Ser Val Leu Ser Ala Asp Gln Leu Phe Ala Pro Gly Val
            260                 265                 270

Lys Met Met Arg Thr Asn Gly Phe Asn Ala Ser Tyr Thr Thr Leu Ala
        275                 280                 285

Glu Gly Ala Asn Ile Pro Ser Lys Tyr Leu Arg His Met Arg Asn Cys
    290                 295                 300

Gly Gly Val Ala Leu Asp Leu Met Gly Met Lys Arg Ile Lys Asn Ser
305                 310                 315                 320

Pro Glu Gly Ala Lys Ser Lys Ile Phe Ser Ile Ile Gln Lys Lys Val
                325                 330                 335

Arg Gly Arg Cys Arg Thr Glu Glu Gln Arg Leu Leu Thr Ser Ala Leu
            340                 345                 350

Lys Ile Ser Asp Gly Glu Asn Lys Phe Gln Arg Ile Met Asp Thr Leu
        355                 360                 365
```

```
Cys Thr Ser Phe Leu Ile Asp Pro Pro Arg Thr Thr Lys Cys Phe Ile
    370                 375                 380

Pro Pro Ile Ser Ser Leu Leu Thr Tyr Ile Gln Asp Gly Asn Ser Val
385                 390                 395                 400

Leu Ala Met Asp Phe Met Lys Asn Gly Glu Asp Ala Cys Arg Ile Cys
                405                 410                 415

Arg Glu Ala Lys Leu Lys Val Gly Val Asn Gly Thr Phe Thr Met Ser
            420                 425                 430

Val Ala Arg Thr Cys Val Ala Val Ser Met Val Ala Thr Ala Phe Cys
        435                 440                 445

Ser Ala Asp Ile Ile Glu Asn Ala Val Pro Gly Ser Glu Arg Tyr Arg
    450                 455                 460

Ser Asn Ile Lys Ala Asn Thr Thr Lys Pro Lys Lys Asp Ser Thr Tyr
465                 470                 475                 480

Thr Ile Gln Gly Leu Arg Leu Ser Asn Val Lys Tyr Glu Ala Arg Pro
                485                 490                 495

Glu Thr Ser Gln Ser Asn Thr Asp Arg Ser Trp Gln Val Asn Val Thr
            500                 505                 510

Asp Ser Phe Gly Gly Leu Ala Val Phe Asn Gln Gly Ala Ile Arg Glu
        515                 520                 525

Met Leu Gly Asp Gly Thr Ser Glu Thr Thr Ser Val Asn Val Arg Ala
    530                 535                 540

Leu Val Lys Arg Ile Leu Lys Ser Ala Ser Glu Arg Ser Ala Arg Ala
545                 550                 555                 560

Val Lys Thr Phe Met Val Gly Glu Gln Gly Lys Ser Ala Ile Val Ile
                565                 570                 575

Ser Gly Val Gly Leu Phe Ser Ile Asp Phe Glu Gly Val Glu Glu Ala
            580                 585                 590

Glu Arg Ile Thr Asp Met Thr Pro Asp Ile Glu Phe Asp Glu Asp Asp
        595                 600                 605

Gln Glu Glu Glu Asp Thr Asp Ile
    610                 615

<210> SEQ ID NO 3
<211> LENGTH: 16
<212> TYPE: PRT
<213> ORGANISM: Infectious salmon anemia virus

<400> SEQUENCE: 3

Ser Arg Pro Lys Arg Ser Asp Tyr Arg Lys Gly Gln Gly Ser Lys Cys
  1               5                  10                  15

<210> SEQ ID NO 4
<211> LENGTH: 16
<212> TYPE: PRT
<213> ORGANISM: Infectious salmon anemia virus

<400> SEQUENCE: 4

Cys Ile Glu Phe Asp Glu Asp Asp Gln Glu Glu Glu Asp Thr Asp Ile
  1               5                  10                  15

<210> SEQ ID NO 5
<211> LENGTH: 18
<212> TYPE: DNA
<213> ORGANISM: Infectious salmon anemia virus
<220> FEATURE:
<221> NAME/KEY: primer_bind
<222> LOCATION: (1)..(18)
```

-continued

```
<400> SEQUENCE: 5
caggtgggag tggcatgg                                                   18

<210> SEQ ID NO 6
<211> LENGTH: 20
<212> TYPE: DNA
<213> ORGANISM: Infectious salmon anemia virus
<220> FEATURE:
<221> NAME/KEY: primer_bind
<222> LOCATION: (1)..(20)

<400> SEQUENCE: 6
agacttggct ccttccggtg                                                 20

<210> SEQ ID NO 7
<211> LENGTH: 28
<212> TYPE: DNA
<213> ORGANISM: Infectious salmon anemia virus
<220> FEATURE:
<221> NAME/KEY: primer_bind
<222> LOCATION: (1)..(28)

<400> SEQUENCE: 7
cgggatccat ggccgataaa ggtatgac                                        28

<210> SEQ ID NO 8
<211> LENGTH: 30
<212> TYPE: DNA
<213> ORGANISM: Infectious salmon anemia virus

<400> SEQUENCE: 8
ggggtacctg cagtttcaaa tgtcagtgtc                                      30
```